United States Patent [19]

Hediger

[11] Patent Number: 4,479,861

[45] Date of Patent: Oct. 30, 1984

[54] METHOD AND APPARATUS FOR PREPARATIVE GEL ELECTROPHORESIS

[76] Inventor: Matthias Hediger, 25 Old Mountain Rd., Farmington, Conn. 06032

[21] Appl. No.: 515,064

[22] Filed: Jul. 19, 1983

[30] Foreign Application Priority Data

Jul. 23, 1982 [CH] Switzerland ............................ 4521/82

[51] Int. Cl.³ .................................................. G01N 27/28
[52] U.S. Cl. .............................. 204/180 G; 204/299 R
[58] Field of Search ............ 204/180 G, 180 R, 299 R, 204/301, 300 R

[56] References Cited

U.S. PATENT DOCUMENTS 3,346,479  10/1967  Natelson ........................ 204/299 R
3,375,187   3/1968  Buchler ......................... 204/299 R
3,539,493  11/1970  Dorman ......................... 204/299 R Primary Examiner—John F. Niebling
Assistant Examiner—B. J. Boggs, Jr.
Attorney, Agent, or Firm—Walter C. Farley

[57] ABSTRACT

A preparative gel electrophoresis apparatus comprises a first outer coolable cylinder, a second inner coolable cylinder within the outer cylinder, a compact column of separating material placed between the first and second cylinders and electrodes arranged above and below the separating column for forming an electrical field over the volume of the separating column, axially translatable adapters above and below the support, surrounding the electrodes, containing duct systems and completely surrounding the inner coolable cylinder. A method of forming the gel column by injecting gel while separating the adapters is also disclosed.

22 Claims, 10 Drawing Figures

METHOD AND APPARATUS FOR PREPARATIVE GEL ELECTROPHORESIS

This invention relates to an apparatus for preparative gel electrophoresis including concentric coolable cylinders and axially translatable end members defining a separating column chamber, and to a method of forming a gel column.

BACKGROUND OF THE INVENTION

Polyacrylamide gel electrophoresis (PAGE) is one of the most effective methods known for the analytical separation of proteins and peptides. However, the preparative procedure of PAGE, which should permit the separation of larger quantities of substances into their mixture components is often made difficult by technical problems. Using a gel layer which is approximately 3 mm thick, the widely used slab gel electrophoresis process permits substance charges up to 13 mg of protein per square centimeter, but the separating resolution is inferior, this being an inherent problem of slab gel electrophoresis due to the unavoidable boundary effects. In general, equipment used for slab gel electrophoresis, which is generally preferred for analytical purposes, has at best a semipreparative capacity with regard to the material density and quantity to be transported.

An apparatus for preparative column electrophoresis is known, for example, from U.S. Pat. No. 3,375,187, Buchler. This patent discloses a system in which the separation of substance mixtures is accomplished in a hollow cylindrical gel column which is introduced between an outer cylinder with a cooling jacket and an inner cooled probe or cold finger. The gel column in this apparatus is mounted in an electrical field, and the electrophoretical separation of peptide material usually proceeds according to plan until the beginning of elution of the material to be separated. When elution of the mixture components begins, there is a tendency for the separated substance bands to successively and asymmetrically "run into" the elution which, in the case of geometrically close separation, leads to partial mixing. In other words, the separated substances are mixed together when there is limited spacing between bands. The apparatus also has a tendency toward incomplete elution and attempts have been made to remove this deficiency by increasing the liquid flow. The resulting undesired dilution of the samples has the effect of preventing the detection of certain substances. For example, continuous UV detection in the range around 280 nm of peptide material is disturbed to the extent that the measurement becomes unusable. The elution liquid also is subject to bubbling, but a debubbler associated with that system helps to combat this problem. It is also disadvantageous that the cooling in the lower column section reserved for elution is not adequate for a number of separating problems. In addition, manipulation with the described apparatus is very complicated, particularly if a gradient gel is to be poured.

BRIEF SUMMARY OF THE INVENTION

Accordingly, an object of the present invention is to provide an apparatus which can be used to accomplish completely satisfactory separating results in preparative gel electrophoresis even with relatively large substance charges and even with small separating gaps between the components to be separated.

A further object is to provide an apparatus which has better separating capacity, in view of the limited dimensions of a separating column, and to bring about increased operational reliability in view of the not infrequently long-term separating processes.

Yet another object is to provide an apparatus which makes it possible to very accurately replace the gel column used in the electrophoresis equipment after it has become exhausted.

Briefly described, the invention comprises an apparatus for preparative gel electrophoresis comprising an outer coolable cylinder; an inner coolable cylinder within said outer cylinder; and upper and lower adapters between said inner and outer cylinders, each of said adapters being axially movable and having means forming fluid seals between said adapter and said cylinders, electrode means connectable to a source of electrical energy for forming an electric field between said adapters, and duct means in each of said adapters for conducting fluids into and out of said adapters to comprise an electrode and elution buffer rinsing system, said outer and inner cylinders and said upper and lower adapters defining a chamber for receiving a column of separating material through which said electric field passes.

In another aspect, the invention includes a method of forming a gel column for preparative electrophoresis comprising providing inner and outer coolable cylinders and a lower end adapter at the bottom thereof forming an annular chamber; providing a source of polymerizable gel having selectable characteristics; providing an upper end adapter which is movable between the upper end of the cylinders and a position adjacent the lower end adapter; conducting polymerizable gel solution under pressure from the gel source into the space between the adapters and the cylinders while concurrently elevating the upper adapter, thereby building a gel column in the chamber, until the desired column height is reached; and allowing the gel to polymerize. Gel gradients can be formed by using a gradient mixer as a gel source.

In order that the manner in which the foregoing and other objects are attained in accordance with the invention can be understood in detail, particularly advantageous embodiments thereof will be described with reference to the accompanying drawings, which form a part of this specification, and wherein.

DETAILED DESCRIPTION OF PREFERRED EMBODIMENTS

Figure 1:
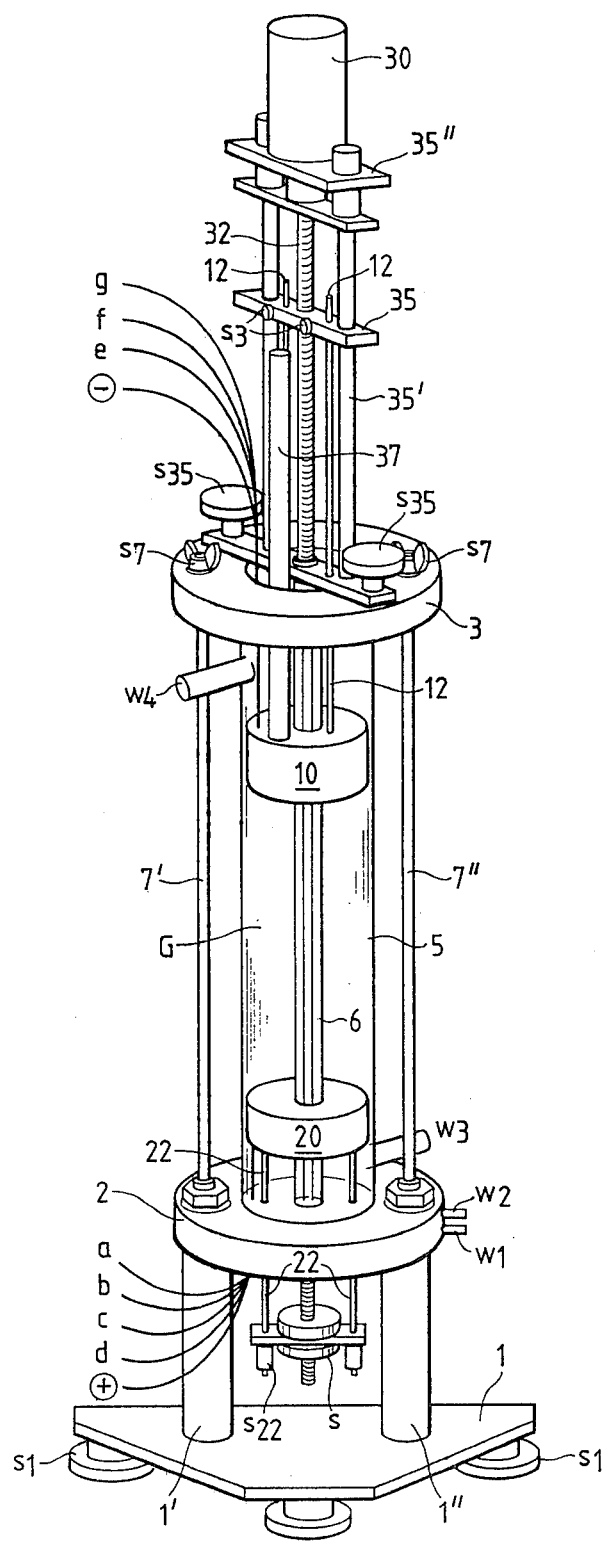
FIG. 1 is a somewhat simplified perspective view of an apparatus in accordance with the invention showing the overall relationships of components.

FIG. 1 provides an overall view of the PAGE apparatus in accordance with the invention. The entire apparatus is supported on a structure base 1 which has support posts 1' and 1" extending upwardly therefrom, the base 1 being level by means of adjustment screws $s_1$. A lower support plate 2 is mounted on support posts 1', 1" and supports an outer glass cylinder 5 which is a type of cylinder supplied with a cooling jacket, not specifically shown in FIG. 1. At the upper end of cylinder 5 is an upper support plate 3, plates 2 and 3 being formed from methylmethacrylate (Plexiglass). The interior volume of cylinder 5 contains a concentric inner glass cylinder 6 which is also a double-walled apparatus which can be supplied with a coolant to function as a cold finger. The exterior of inner cylinder 6 and the interior of outer cylinder 5 define an annular cylindrical chamber to receive the separating gel G. Preferably, the length of both of the glass cylinders is approximately 350 mm, the internal diameter of the outer glass cylinder with its cooling jacket is approximately 45 mm, and the external diameter of the cold finger 6 is approximately 16 mm.

The apparatus further includes a lower adapter 20 which is contained within cylinder 5 and is axially or longitudinally movable therein, and an upper adapter 10 which is similarly contained within cylinder 5 and is axially movable. Thus, the actual gel chamber G is defined longitudinally between these two adapters. Support plates 2 and 3 are interconnected by two tie rods 7' and 7", upper plate 3 being attached thereto in a manner to clamp the ends of glass cylinder 5 by wing nuts $s_7$. Outer glass cylinder 5 has a coolant inlet $w_3$ and a coolant outlet $w_4$. The coolant for the cold finger is preferably supplied thereto through ducts or channels in the lower support plate 2 which connect with inlets and outlets $w_1$ and $w_2$, respectively.

Adaptors 10 and 20 have a multilayer structure which will be described in greater detail hereinafter in connection with FIGS. 2–5. The lower adapter 20 is longitudinally movable over a relatively small distance in the lower part of cylinder 5 and cold finger 6. For this purpose, two guide members 22 extend axially through lower support plate 2 and are fixedly attached to adapter 20. The lower ends of guide members 22 are attached by assembly screws $s_{22}$ to a small adjustment plate which can be raised or lowered with respect to the glass cylinders by means of set screws s threadedly engaging a threaded shaft extending downwardly from plate 2. A plurality of feed and discharge lines a, b, c, and d for delivering and extracting electrolyte buffer solutions or elution buffer solutions extend through plate 2 and into adapter 20, along with a conductor for connection to a positive electrode within adapter 20. Lines a–d are tubing and the positive conductor is connectable to the positive terminal of a power supply, not shown.

Upper adapter 10 is also axially displaceable in cylinder 5 and can be moved over the entire length of the gel chamber. Thus, adapter 10 also includes guide members 12 which extend axially upwardly from adapter 10, the upper ends of guides 12 being connected to an upper support structure including a plate 35, guide rods 35' and a mounting plate 35". A motor 30 which is of a conventional variable speed type is mounted on plate 35" and drives a threaded rod 32 which threadedly engages mounting plate 35 and is therefore able to move plate 35 upwardly and downwardly, carrying with it guide members 12 and adapter 10. Plate 35 is attached by screws $s_{35}$ to the upper support plate 3. Feed and discharge lines g, f, and e for the electrode buffer as well as for gel inlet when preparing or treating the gel column extend through upper plate 3 to adapter 10. Also, a conductor extends therethrough for connection to a negative electrode in adapter 10. In addition, adapter 10 contains an opening h for supplying the solution which is to be separated by the gel column. This opening can be closed by means of a plug pin 37. It is important to note that both adapters are provided with O-ring seals or the like to form a secure fluid seal between the exterior of each adapter and the interior of cylinder 5, as well as the interior of each adapter and the exterior of cold finger 6.

Figure 2:
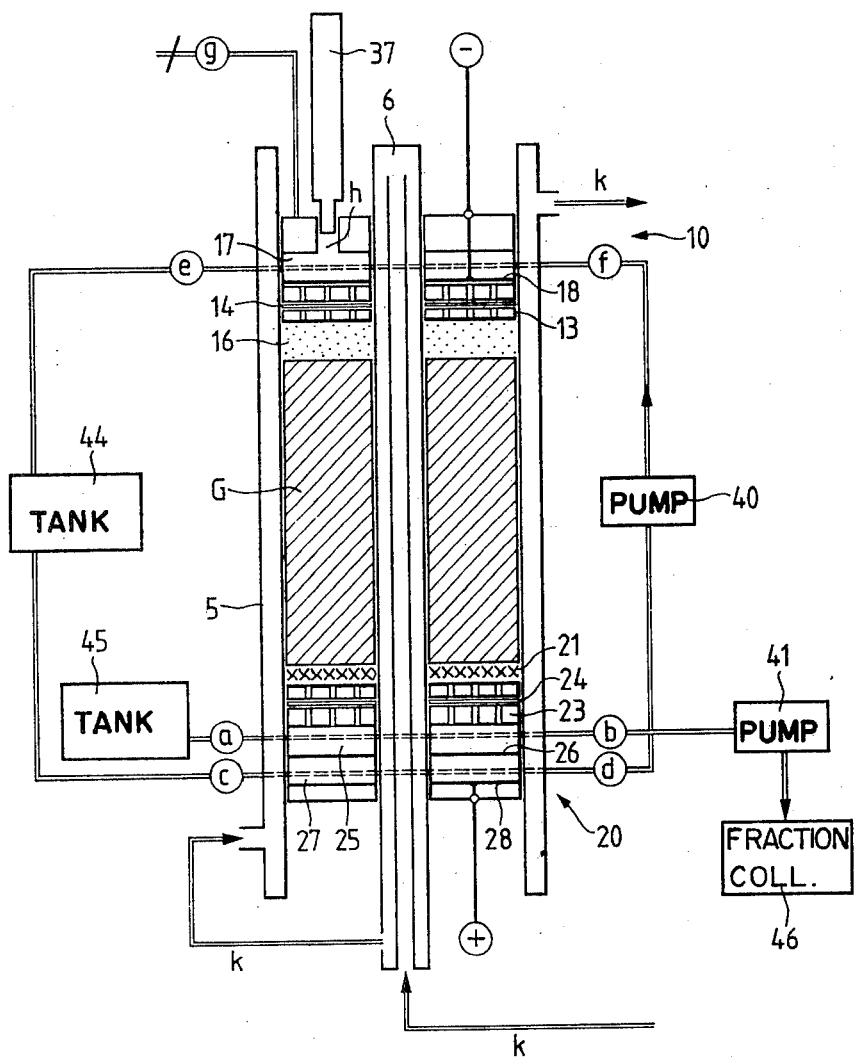
FIG. 2 is a schematic side elevation diagrammatically illustrating the interrelationship and operation of the components of the apparatus of FIG. 1.

FIG. 2 diagrammatically shows the arrangement and operation of the preparative polyacrylimide gel electrophoresis apparatus. The volume-adjustable gel chamber is, as shown, formed between outer cylinder 5, inner cold finger 6, lower adapter 20 and upper adapter 10. The two adapters are provided with electrical conductors in ducts in which circulate the electrode buffer. In this case, the electrode buffer is shown to be circulating in a counterclockwise direction under the influence of a pump 40. The electrode buffer flows out of a collecting tank 44 and through inlet c into the electrode buffer duct of lower adapter 20 and passes out of outlet d, through the pump and into inlet f of upper adapter 10 into the electrode buffer duct thereof and then out of outlet e to flow back into the electrode buffer collecting tank 44. The electrode buffer circulation also serves to cool the electrodes which is not generally achieved by the cooling of the inner and outer cylinders. Any gas bubbles formed during electrolysis can be collected in a separate gas collector during the electrolysis operation without it being necessary to open the system to the outside. It is specifically emphasized at this stage that, unlike the prior art, the apparatus in accordance with the invention comprises a closed system. The term "closed system" is understood to mean that the complete liquid conducting system, i.e., the buffer system comprising the electrode buffer, elution buffer, separating column, all ducts, lines, and the like, are either closed circulation systems in themselves or include liquid supply displacements with conventional liquid seals.

A second pump 41 feeds the elution buffer out of a collecting tank 45 through an inlet a and through the elution duct in the lower adapter 20 to outlet b and, from there, into, for example, a fraction collector 46. A more detailed description of the various ducts for the electrode buffer circulation and for the flow of the elution buffer will be given in connection with FIG. 3 which shows the construction of the two adapters. The coolant flow through cold finger 6 and through the cooling jacket of glass cylinder 5 is indicated by arrows k joining the cooling systems. FIG. 2 also shows upper adapter 10 to have two feed lines g and h, line g being used for feeding in the gel solution when building up the gel column, and opening h being used to supply the sample mixture. As in the case of FIG. 1, feed line h can be closed by a rod-like plug pin 37.

Figure 3:
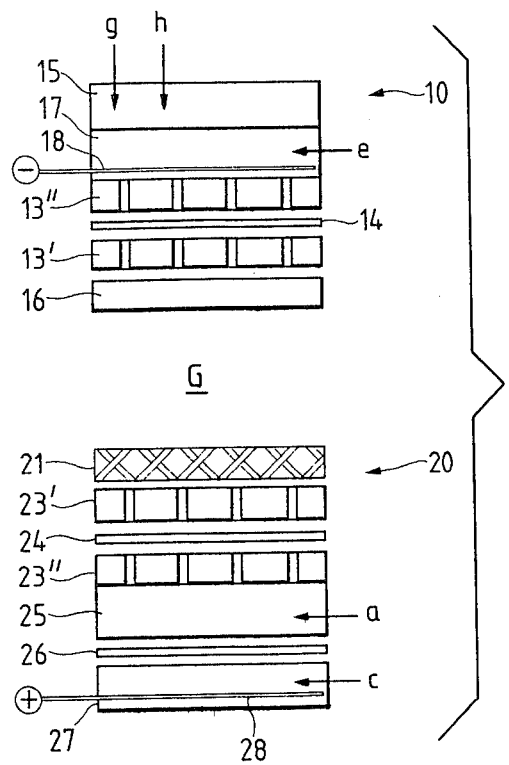
FIG. 3 is a schematic side elevation, partly exploded, of the upper and lower adapters usable in the apparatus of FIGS. 1 and 2.

FIG. 3 shows the details of the construction of adapters 10 and 20, the adapters being shown in approximately the relationship they occupy within cylinder 5, but each adapter being slightly "exploded" so that the individual components are separated and more easily seen. The upper adapter includes an adapter head 15 with an electrolyte buffer duct 17 formed therein. This electrolyte buffer duct also contains a platinum electrode 18 having a connection to the external negative terminal of a power supply. Inlet g for the gel liquid for building up the gel column and inlet 8 for the product to be separated also lead into the adapter head. A further inlet, to be described hereinafter, is used for the introduction of the electrolyte buffer represented by the arrow e. The electrolyte duct is terminated at the bottom by a perforated plate or strainer 13" which has a counterpart plate, also a perforated plate or strainer 13', between which is secured a filter element 14, preferably a Durapor filter manufactured by the Millipore Corporation. This buffer-saturated filter performs an electrical function with respect to a buffer-filled intermediate space 16 which is positioned above the prepared gel column. Gel chamber G, which rests on the top of lower adapter 20, starts below the buffer-filled intermediate space 16 of the column.

Considered in order from the gel chamber, the lower adapter is constructed as follows. A grid plate 21, which is preferably formed from a wide-mesh nylon netting, forms an intermediate space in much the same way as the buffer-filled space 16 and is placed above a perforated plate or strainer 23' which has a counterpart plate or strainer 23" between which is a filter element 24 which is chosen in such a way that the separated products can pass through it without difficulty. It is again preferable to use a Durapor filter as filter 24. The two perforated plates 23', 23" with the intermediate filter element are placed adjacent the elution duct in a body 25 which has an inlet for the elution buffer as indicated by arrow a. Below the elution duct, and terminating that duct, is a dialysis membrane 26 which has the primary function of maintaining electrical contact with the electrolyte buffer in the electrode space. However, the dialysis membrane must also prevent the passage of molecules of the separated product. Below dialysis membrane 26 is arranged the electrolyte buffer duct 27 in which a platinum electrode 28 is placed, the electrode having provision for connection to a positive terminal of a power supply which is external to the apparatus. Arrow c represents the electrolyte buffer inlet into duct housing 27 which, in the manner shown in FIG. 2, provides for flow around the platinum electrode. The same buffer then flows on and finally passes into the electrolyte buffer duct 17 at inlet e in the upper adapter 20. The cross section of the membrane over which the product flows should be minimized in order to prevent any absorption of the separating substance by the membrane.

Thus, the lower adapter comprises two superimposed duct systems 25, 27, duct system 27 being washed thoroughly with electrode buffer during electrophoresis and providing the contact to the power supply device via platinum electrode 28. Duct system 25 is used as an elution chamber and is thoroughly washed by elution buffer during electrophoresis. The capacity of the duct system used as the elution chamber is approximately 1 ml in an embodiment having dimensions such as those given above. As stated, the two duct systems are separated by a dialysis membrane which, although permitting electrical contact, is impermeable to, for example, peptides and proteins.

An intermediate space, the minimum height of which is determined by grid plate 21, is provided between the lower adapter and the gel column which extends above it. The Durapor filter used in the adapter is completely permeable to, for example, peptides and proteins, and also constitutes a communication passage for electrical contact from the electrode chamber to the gel column, but prevents mixing of the elution buffer in the intermediate space produced by grid plate 21.

The significance of this intermediate space is the production of a symmetrical electrical contact over the entire lower gel half which ensures elution of the bands separated in the gel without any deformation. Consequently, the products separated in the gel first pass into the intermediate space of grid plate 21 and are then transferred into duct system 25 at a speed which is much higher than the transport speed in the gel and the products are then taken up by the elution buffer flowing therein and are transported away to, for example, a fraction collector.

The upper adapter has two functions. First, it serves as an auxiliary element during gel pouring or casting. Additionally, it acts as the upper counterelectrode. As an auxiliary element during gel pouring, the upper adapter makes it possible to overlay solutions, i.e., to arrange solutions having different densities in layers and to pour gel gradients. The special building up of a gel column, i.e., gel pouring, will be described in detail hereinafter.

Figure 4A:
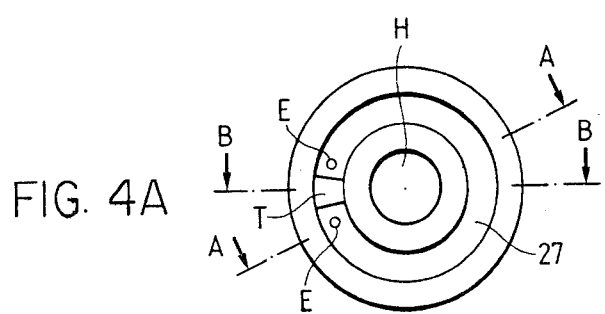
FIG. 4A is a bottom plan view of a typical duct arrangement in one of the adapters of FIG. 3.
Figure 4B:
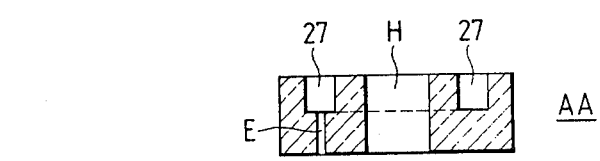
FIGS. 4B and 4C are, respectively, sectional views along lines A—A and B—B of FIG. 4A.
Figure 4C:

FIG. 4A shows a plan view of a duct structure such as duct 27. Preferably, the duct is formed from a solid circular plexiglass plate by initially drilling a hole in the center to form an opening H for the cold finger, followed by the cutting of a concentric duct 27. The cutting can be accomplished in such a way that it extends around less than 360°, leaving a partition T. Alternatively, the duct can be cut as a complete annular passageway followed by the insertion of partition T as a separate body. Inflow and outflow ports E make it possible to allow the buffer to flow in through one of the ports E close to partition T, filling the entire duct and then flowing out again at the outlet. FIG. 4B shows a section A—A through the duct structure in which an electrolyte buffer c, which passes into the duct chamber. A second section B—B is taken through the partition to show that the duct system is blocked at this point. The dialysis membrane 26, for example, is placed above the duct system and then the duct system 25 is positioned above that for the elution buffer. Duct system 25 would, in this case, have partition T but would be open to the top and bottom. Thus, the inlets and outlets would be directed radially inwardly through the edge of the duct. Perforated plate 23 with filter element 24 placed over duct system 25 allows the eluent to pass into the elution duct at all points where there are holes. This ensures an outflow of the eluent from the separated bands over the entire cross section and in a completely uniform flow pattern so that the bands to be eluted are not distorted by different flow or transport speeds distributed over the cross section.

Figure 5:
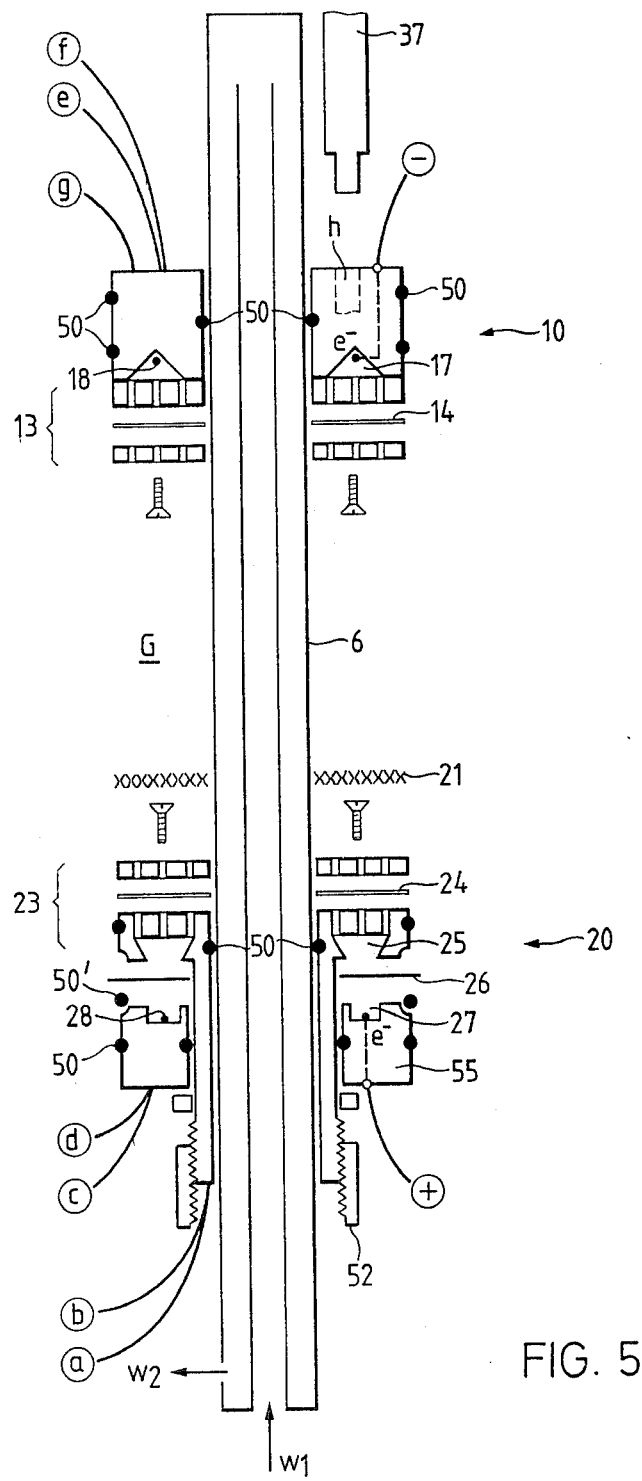
FIG. 5 is a schematic side elevation, partially exploded, showing the interrelationship of the adapter and inner cylinder components of the apparatus in greater detail and showing modified forms of the adapter structure.

FIG. 5 shows a different view of the adapters 10 and 20 which have a slightly different structure from those diagrammatically illustrated in FIG. 3. Starting with upper adapter 10, it can be seen that the adapter is sealed against the inner and outer cylinders by O-rings 50 and is longitudinally displaceable. Cylinder 5 is omitted from FIG. 5. The electrolyte buffer duct 17 is formed as an annular slot or groove which is triangular in cross section, the open base of which being terminated by perforated plate pair 13 with the intermediate filter element 14 being attached between the plates. The plates are then held together with a screw, as illustrated.

The lower adapter is also longitudinally displaceable and, in this embodiment, a system of concentric components permits simple mounting and attachment of the adapter parts. The perforated plate 23" connected to elution duct 25 (FIG. 3) is formed in one piece with an annular groove for the duct. A longitudinally displaceable companion part 55 having an annular duct 27 for the electrolyte buffer can be pressed against membrane 26 and elution duct 25 by means of a box nut 52 in such a way that a complete seal to the outside is formed with the aid of a further O-ring 50'. The components are formed from materials which are chosen to be adequate as a function of the requirements. In the present embodiment, plexiglass was used partly because it is easily workable.

Figure 6:
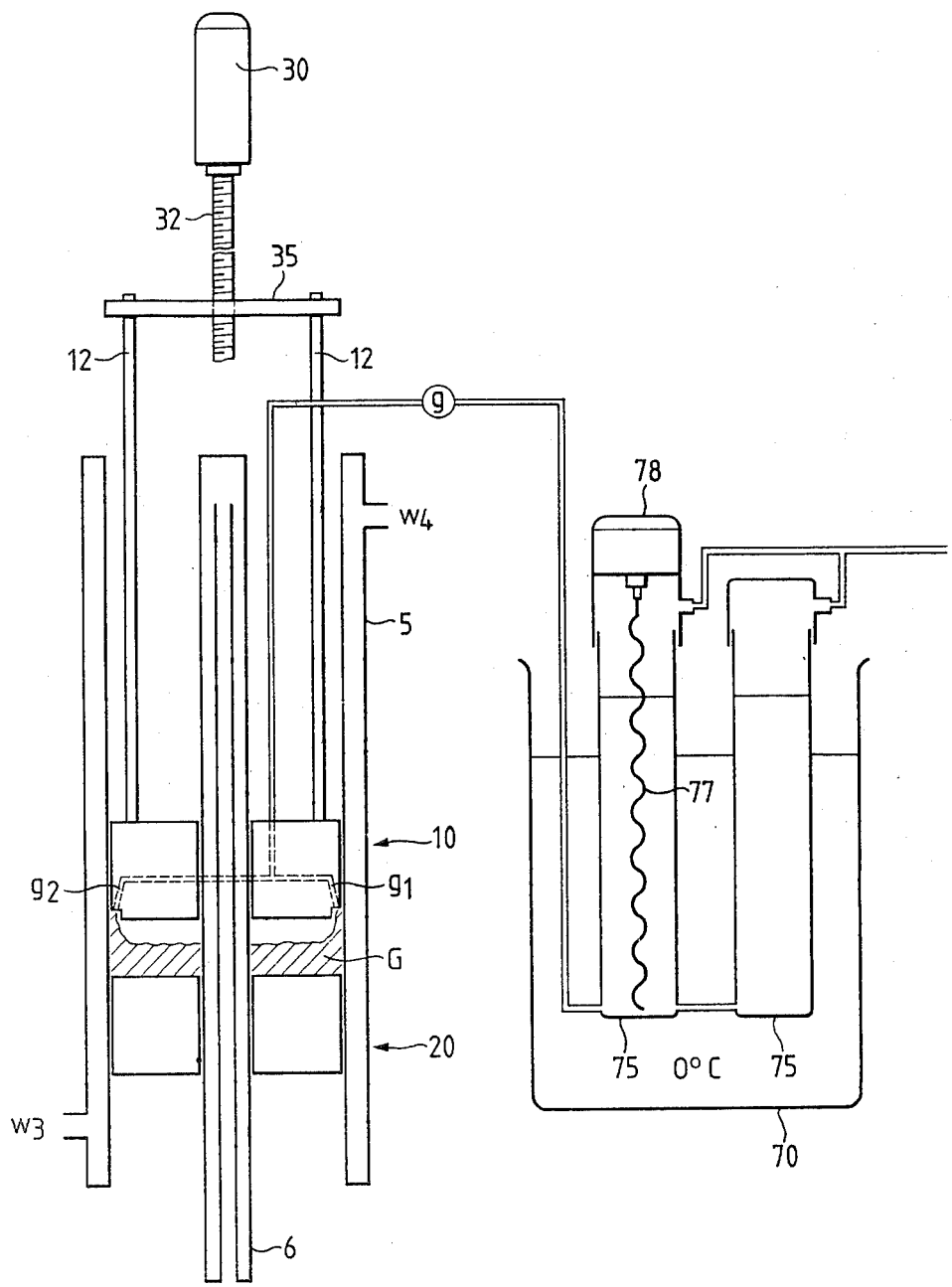
FIG. 6 is a schematic side elevation of an arrangement for filling the separation chamber of the apparatus in accordance with the invention.

An apparatus which is usable to accomplish the method of gel pouring or casting is shown in FIG. 6. Portions of the preparative gel electrophoresis apparatus as herein described is diagrammatically shown on the left. In this simplified drawing, the basic components are recognizable including glass cylinder 5 with its cooling jacket and the cooling water connections $w_3$, $w_4$; the inner cold finger 6; the upper support structure 35 with electric motor 30; and threaded rod 32 which is driven by the motor 30 to raise and lower upper adapter 10. Lower adapter 20 remains stationary during the pouring process. It can be seen that the two adapters are initially positioned closely adjacent to each other in order to build up the gel column between them by slow, axial separation. FIG. 6 shows the process after it has begun as evidenced by the existence of a portion G which has been formed. The gel is introduced into the gel chamber by means of an inlet conduit g which connects with two or more ducts $g_1$, $g_2$, $g_n$, the gel being supplied from a gel preparation device (gradient mixer) shown to the right of the drawing. The preparation device essentially comprises a cooling bath 70 and a communicating pair of vessels 75 containing the gel solution, one of the vessels also containing a stirrer 77 driven by a motor 78. Both communicating vessels are under a slight overpressure of preferably 0.8 atm gauge pressure. This overpressure is best achieved by nitrogen. Prior to gel pouring, the complete system, including the separating means, must be pressurized. If the upper adapter 10 is then slowly drawn upwardly by motor 30, the gel solution flows from the gradient mixer through conduit g, through outlets $g_1$, $g_2$ . . . $g_n$, along the outer glass wall, into the space between the upper and lower adapters which define the enlarging gel chamber. There is thus a continuous arrangement in layers without the previously poured solution being agitated. The overpressure of 0.8 atm is used because, when the upper adapter is raised, it is possible for an underpressure to form which would lead to the formation of air bubbles. Thus, the pressure prevents disturbing cavitation.

As previously mentioned, the upper adapter also has an opening h, not shown in FIG. 6, through which it is possible to apply the material to be separated by a pipette coupled to a tube. This opening can subsequently be closed by a plug 37.

Figure 7:
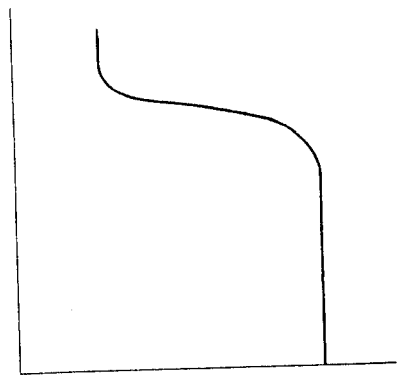
FIG. 7 is a diagram illustrating the gel system with a gel gradient in accordance with the invention used in the apparatus of FIGS. 1, 2 and 5.

An example of a gel system for the separation of proteins and peptides in sodium dodecyl sulphate is shown in FIG. 7. For separation purposes, use was made of the gel system of Ornstein and Davis, modified by Lämmli and with the following additional modification. The discontinuous transition between the separating column and the stacking gel was replaced by a gel gradient such as shown in FIG. 6. With the dimensions previously given, the gel column is approximately 200 ml subdivided into 25 ml of 3% by weight stacking gel, 30 ml of gel gradient between the separating and the stacking gel, and finally approximately 145 ml of 15% by weight of separating gel.

Using the above described apparatus and the given process, it is very easy to produce a gel gradient according to FIG. 6. An example of an operating sequence using the apparatus in accordance with the invention can be summarized in the form of the following nine operating steps.

1. Equip the upper adapter 10 with a Durapor filter, attach the adapter to the upper support structure 35 using screws $s_3$. Connect the power supply cable.

2. Equip the lower adapter 20 with a dialysis membrane, mount the adapter with screws $s_{22}$ onto the lower part of the apparatus and connect the power supply cable to the adapter. Using tubes a through d, fill adapter 20 with 20% sucrose solution. Equip the adapter with a Durapor filter and place the nylon netting 21 on the adapter.

3. Attach cold finger 6 and the outer glass cylinder 5 between support plates 2 and 3 using nuts $s_7$.

4. Introduce 5 ml of 20% sucrose solution and then fix the upper support structure with upper adapter 10 to the main frame by using screws $s_{35}$. Provide adapter 10 with the power supply cable and lower the upper adapter until it is approximately 2 cm above the lower adapter 20 using motor 30.

5. Set the cooling systems to the desired temperature and, with an overpressure of approximately 0.8 atm, pour the gel as shown in FIG. 6 and then overlay with a little water. Interrupt the cooling system and at 0.8 atm with rising temperature, preferably ambient temperature, allow polymerization to take place.

6. Release the pressure by opening tube e. Following pressure balance, rinse the gel surface with water and, for forming space 16, cover with approximately 50 ml of electrode buffer until opening h is flooded.

7. Pass the sample to be separated onto the gel surface through opening h using a pipette extended by a tube.

8. Produce electrode buffer circulation and continuous elution washing in accordance with FIG. 2 and bring the cooling system to the desired temperature.

9. Connect the electrical cables of both adapters to the power supply and turn on the power.

As an alternative to the use of the pressure differential described in step 5, a pump can be employed in conduit g to transfer the material. In this arrangement as with the overpressure technique for creating the pressure differential, the upper adapter can be forced upwardly by the pressure in the column.

Figure 8:
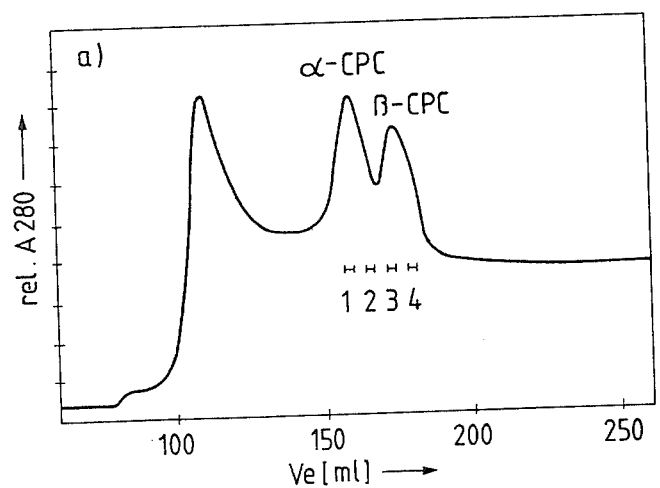
FIGS. 8A and 8B are simplified illustration of, respectively, an electrophoretic diagram and an absorption band diagram illustrating an example of separation in connection with C-phycocyanin from cyanobacterium *Mastigocladus laminosus*.
Figure 8:
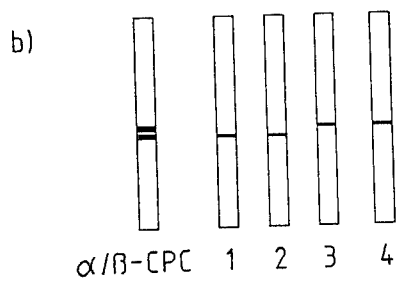

In order to check the separating characteristics of the apparatus for preparative gel electrophoresis, the alpha and beta chains of C-phycocyanin from the cyanobacterium *Mastigocladus laminosus* were used as the test mixture. These light-harvesting proteins have covalently bound chromophores and can therefore be directly observed during separation. The two alpha and beta chains consist, respectively, of 162 and 172 amino acids, corresponding to a molecular weight difference of approximately 5.8%. The two bands of the C-phycocyanin chains passed as horizontal bands through the gel into the lower adapter where they were washed out with the continuous elution system. The graph of FIG. 8A and the gels of the marked fractions represented below that graph in FIG. 8B show the separation of C-phycocyanin into the two subunits alpha and beta. It is also clear that the apparatus in accordance with the invention makes it possible to carry out separations with a similar resolution to that of analytical gel electrophoresis.

The apparatus for preparative gel electrophoresis in sodium dodecyl sulphate (SDS) makes it possible to separate hydrophilic and hydrophobic peptides and proteins. The separating possibilities were demonstrated by various experimental examples such as the separation of alpha/beta-chains of C-phycocyanin from cyanobacterium *Mastigocladus laminosus*, the purification of clostripain fragments of LDH from *B.subtilis* (BX1) and the isolation of subunits of reaction centers of *Rhodopseudomonas viridis*. The yield of purified peptides and proteins was more than 70%. Automatic amino acid sequence analysis of clostripain fragments Clpl permitted sequencing up to the 50th degradation cycle without difficulty and revealed that peptides and proteins obtained by this method are suitable for automatic Edman degradation.

Peptides and proteins can be separated from the most varied molecular weight ranges through a suitable choice of the acrylamide concentration. The upper acrylamide concentration limit was approximately 25% and permitted the separation of peptides down to a molecular weight of approximately 3,000 to 4,000. The lower acrylamide concentration limit is about 6%. (The gel becomes soft and greasy with a too low acrylamide concentration).

An important problem in the prior art preparative gel electrophoresis apparatuses was the incomplete elution of the protein bands separated in the gel. The elution is often improved by high washing speeds with elution buffers, but this led to extreme dilution of the eluted bands and did not permit detection at 280 nm. Experiments with the apparatus in accordance with the invention has shown that with an elution rate of 10 ml per hour, there were no resolution losses caused by incomplete elution. It was generally relatively easy to follow separation by detection at 280 nm.

In gel electrophoresis, the collecting gel method permitted the application of relatively large sample volumes to the gel. However, with larger gels, the problem existed that the intermediate phase between the stacking gel and the separating gel was usually deformed after polymerization. It was possible to circumvent this problem with the aid of the device for pouring gel gradients disclosed herein, in that a gel gradient was introduced between the stacking gel and the upper part of the separating gel. As a result, it was possible to apply sample volumes of up to 15 ml to the gel. The alpha/beta chains of C-phycocyanin dissolved in 5 ml of sample buffer were concentrated in the stacking gel to a sharp, horizontal band and, without deformation, passed through the gel gradient into the separating gel.

Heat dissipation during electrophoresis is decisive for the separation and symmetrical elution of the bands. In particular, two points are decisive for adequate heat dissipation. One is that the cooling jacket and cold finger project beyond the two adapters so that a temperature gradient between the gel and the lower adapter is prevented. The second point is that additional cooling of the two adapters is ensured by the electrode buffer circulation system.

No disturbing air bubbles occurred during electrophoresis when using the preparative PAGE apparatus. The gases formed on the platinum electrode by the hydrolysis of water were effectively washed out by the electrode buffer circulation system.

The apparatus permitted a much easier performance of preparative gel electrophoresis than other available devices. It is not necessary to use additional adapters for pouring the gel, nor to replace the adapters after polymerization. Using the gel pouring device, the gel could be poured directly on to the elution adapter which was covered with a small quantity of sucrose solution. The total time for the start of preparative gel electrophoresis was about 5 hours. Separation in a 15% gel took 1 to 3 days. During this time, the apparatus operated automatically and in a maintenance-free manner.

While certain advantageous embodiments have been chosen to illustrate the invention, it will be understood by those skilled in the art that various changes and modifications can be made therein without departing from the scope of the invention as defined in the appended claims.

What is claimed is:

1. A method of forming a gel column for preparative electrophoresis comprising
   providing inner and outer coolable cylinders and a stationary lower end adapter at the bottom thereof forming an annular chamber;
   providing a source of polymerizable gel solution having selectable characteristics;
   providing an upper end adapter which is movable between the upper end of the cylinders and a position adjacent the lower end adapter;
   conducting polymerizable gel solution from the gel source into the space between the adapters and the cylinders while the upper adapter is concurrently elevated, thereby arranging the gel solution in gradients and building a gel column in the chamber, until the desired column height is reached;
   and allowing the gel to polymerize.

2. A method according to claim 1 wherein a differential pressure is produced between said source and said chamber.

3. A method according to claim 2 wherein said differential pressure is produced by driving said upper adapter upwardly.

4. A method according to claim 1 and further including a pump for conducting said polymerizable gel solution from said source to said space.

5. An apparatus for preparative gel electrophoresis comprising
   an outer coolable cylinder;
   an inner coolable cylinder within said outer cylinder; and
   upper and lower adapters between said inner and outer cylinders, each of said adapters being axially movable and having
      means forming fluid seals between said adapter and said cylinders,
      electrode means connectable to a source of electrical energy for forming an electric field between said adapters, and duct means in each of said adapters for conducting fluids into and out of said adapters to comprise an electrode and elution buffer rinsing system, said outer and inner cylinders and said upper and lower adapters defining a chamber for receiving a column of separating material through which said electric field passes.

6. An apparatus according to claim 5 wherein said duct means in each adapter includes a plurality of concentrically arranged channels and means for inducing flow in each channel in only one direction.

7. An apparatus according to claim 6 wherein each channel includes a radially extending partition with an inlet to one side and an outlet to the other side of said partition.

8. An apparatus according to claim 6 wherein, in said upper adapter, said electrode means includes an electrode in an electrode buffer duct, said upper adapter further including a first separating member below said electrode buffer duct for separating said electrode from said column of separating material, and a plurality of inlet passages for conducting separating material into said chamber to initially establish said column such that separating material runs down the glass wall of at least one of said outer and inner cylinders without disturbing material already poured.

9. An apparatus according to claim 8 wherein said inlet passages are arranged symmetrically and open near the bottom of said adapter and are adjacent at least one of the inner and outer edges thereof.

10. An apparatus according to claim 8 wherein said electrode means in said lower adapter includes an electrode in an electrode buffer duct, said lower adapter further including a second selective separating member above said electrode buffer duct, means defining an elution duct above said second separating member, said elution duct being open at the top and bottom, a third selective separating member above said elution duct to separate said duct from said column.

11. An apparatus according to claim 10 and further comprising a liquid-filled area at the interface between each of said adapters and said column.

12. An apparatus according to claim 10 and further comprising drive means for elevating and lowering said upper adapter, said drive means including a motor for elevating said upper adapter while maintaining said lower adapter stationary, and conduit means connectable to a source of liquid and to said first and second inlet passages to permit forming of a plurality of gradients in said chamber as said upper adapter is elevated to establish said column.

13. An apparatus according to claim 12 wherein said column includes a column section for collecting and a column section for separating, separated by a gradient of separating material.

14. An apparatus according to claim 13 wherein said separating material in said column is a gel.

15. An apparatus according to claim 10 wherein said separating material in said column is a gel.

16. An apparatus according to claim 10 wherein said duct means and said chamber comprise a closed liquid system having seals separating said system from the exterior.

17. An apparatus according to claim 8 wherein said separating material in said column is a gel.

18. An apparatus according to claim 8 wherein said duct means and said chamber comprise a closed liquid system having seals separating said system from the exterior.

19. An apparatus according to claim 6 wherein said separating material in said column is a gel.

20. An apparatus according to claim 6 wherein said duct means and said chamber comprise a closed liquid system having seals separating said system from the exterior.

21. An apparatus according to claim 5 wherein said separating material in said column is a gel.

22. An apparatus according to claim 5 wherein said duct means and said chamber comprise a closed liquid system having seals separating said system from the exterior.

* * * * *